United States Patent [19]

Vlock

[11] 4,242,323
[45] Dec. 30, 1980

[54] PLAQUE INHIBITING ORAL COMPOSITION

[76] Inventor: David G. Vlock, 2 E. 65th St., New York, N.Y. 10021

[21] Appl. No.: 68,825

[22] Filed: Aug. 22, 1979

[51] Int. Cl.$^3$ .......................... A61K 7/26; A61K 9/68
[52] U.S. Cl. ....................................... 424/58; 424/48; 426/3; 426/651; 426/593; 426/306; 426/534; 426/631
[58] Field of Search ................................. 424/48–58; 426/3–6, 306, 534, 593, 631, 651

[56] References Cited

U.S. PATENT DOCUMENTS

| | | | |
|---|---|---|---|
| 1,206,467 | 11/1916 | Reid | 426/3 |
| 1,275,779 | 8/1918 | Spies et al. | 424/49 |
| 1,416,242 | 5/1922 | Steinemann | 424/49 |
| 1,522,410 | 1/1925 | Bluhm et al. | 424/58 |
| 1,527,523 | 2/1925 | Nitardy et al. | 424/58 |
| 1,591,727 | 7/1926 | Nitardy | 424/49 |
| 1,664,182 | 3/1928 | Parisi | 424/58 |
| 1,786,831 | 12/1930 | Dellenbarger | 426/3 |
| 2,224,637 | 12/1940 | Mahle | 426/3 |
| 2,343,651 | 3/1944 | Fielding | 424/49 |
| 3,632,358 | 1/1972 | Echeandia et al. | 426/3 |

FOREIGN PATENT DOCUMENTS

| | | | |
|---|---|---|---|
| 508927 | 1/1927 | Fed. Rep. of Germany | 424/49 |
| 1098166 | 1/1961 | Fed. Rep. of Germany | 424/49 |
| 2523940 | 9/1976 | Fed. Rep. of Germany | 424/49 |
| 540071 | 7/1922 | France | 424/49 |
| 721271 | 3/1932 | France | 424/49 |
| 833550 | 10/1938 | France | 424/49 |
| 1381416 | 11/1964 | France | 424/49 |
| 2345938 | 2/1977 | France | 426/3 |
| 495131 | 6/1954 | Italy . | |
| 49-32069 | 8/1974 | Japan | 426/3 |
| 51-40143 | 1/1976 | Japan | 424/49 |
| 1538750 | 1/1979 | United Kingdom | 426/3 |

OTHER PUBLICATIONS

Jacobs, How To Flavor Tooth Paste, Am. Perfumer & Essent. Oil Rev. 61: 389, 391, 393, (1953).
Jacobs, Flavoring Mouth Washes, Am. Perfumer & Essent. Oil Rev. 61: 469, 471,(1953).
Chem. Abst. 87: 199299d, (1977), Tooth Injury From Acidogenic Sweets, Muehlemann Abstr. of Schweiz. Monatsschr. Zahnheilkd., 1977 87(4): 293–7.
Chem. Abst. 87: 150276e, (1977), Evaluation of the Cariogenicity of Confectionery By Intra-oral Wire Telemetry Imfield, Abstr. of Schweiz. Monatsschr. Zahnheilkd., 1977 87(5): 437–64.
Kirk-Othmer Encyclopedia of Chemical Technology, 2nd Ed., (1964), vol. 5, Chocolate & Cocoa, John Wiley & Sons, pp. 363–365, 377, 378, 381–385, 388–400.
Lord, Everybody's Cookbook, (1937), Harcourt Brace & Co., N.Y., p. 280, Chocolate Mint Sauce; p. 436, Chocolate Peppermint Icing.
Roth, Old-Fashioned Candy Making, Henry Regnery, Chicago, (1974), p. 55, Chocolate Covered Mints.
Grossman's Guide To Wines, Beers & Spirits, 6th Ed., Chas. Scribner Sons, N.Y., (1977), pp. 371–382, Liqueurs and Cordials esp. p. 381, Vandermint Chocolate-Mint Liqueur 60 Proof.
Fenaroli's Handbook Of Flavor Ingredients, 2nd Ed., vol. 2, (1975), CRC Press, Cleveland, Ohio, pp. 611, 618, 620, 653, 760–763, 866–869.

*Primary Examiner*—Shep K. Rose
*Attorney, Agent, or Firm*—Lawrence Rosen

[57] ABSTRACT

Oral compositions possessing plaque inhibiting characteristics containing a combination of cocoa powder and a flavorant selected from peppermint oil, spearmint oil, cinnamon oil, and mixtures therefore. Dentifrices containing only natural ingredients including the cocoa powder and the prescribed flavorant are the preferred plaque inhibiting compositions.

1 Claim, No Drawings

PLAQUE INHIBITING ORAL COMPOSITION

BACKGROUND OF THE INVENTION

The present invention relates to oral compositions containing a combination of plaque inhibiting ingredients, namely cocoa powder and a flavorant selected from the group consisting of peppermint oil, spearmint oil, cinnamon oil and mixtures thereof. More particularly, the invention pertains to compositions, such as dentifrices, which are effective in inhibiting plaque in the oral cavity.

As is well known, plaque is a layer or deposit which forms on the surface of the teeth or adjacent areas if one does not brush or brushes inadequately. Plaque is believed to be a product or microbial growth, primarily derived from food residues in the mouth. Mucoproteins and minerals present in the saliva and dead cells in the mouth also promote plaque formation. Dental experts generally accept that calculus, which is a calcified formation on teeth, originates with plaque; and that clinical supragingival calculus (tartar) is a type of dental plaque which has crystallized with the formation of a hydroxyapatite crystalline structure.

Without adequate brushing the plaque formation on the teeth tends to increase in size and thickness and to adhere more tenaciously. Furthermore, the bacterial metabolism within the plaque on the tooth surface results in production of acids, toxins and enzymes which are deleterious to the neighboring tissues. There is also some evidence indicating plaque as being the direct cause of dental caries, because of the generation of lactic acid within the plaque structure.

It follows that it would be desirable to have oral compositions available which would inhibit or even reduce plaque formation in the oral cavity. The present invention is concerned with this dental problem and provides novel oral compositions which are characterized by anti-plaque properties.

Dentifrices which in general are the preferred oral compositions of the invention are meant to include any conventional cleansing composition such as pastes, creams, mucilaginous liquids and powders. A typical dentifrice will contain as a vehicle about 20–95% by weight of a water-insoluble polishing material, preferably including water-insoluble phosphate such as dicalcium phosphate, tricalcium phosphate, trimagnesium phosphate, calcium pyrophosphate, dimagnesium phosphate and calcium carbonate. The dentifrice may also include water, binders such as glycerine, sorbitol, propylene glycol, and polyethylene glycol 400; gelling agents such as natural and synthetic gums inclusive of gum tragacanth, Irish moss, sodium carboxymethyl cellulose, hydroxyethyl carboxymethyl cellulose, polyvinyl pyrrolidone, starch, water-soluble hydrophilic colloidal carboxyvinyl polymers, such as those sold under the trademark "Carbopol", and synthetic inorganic silicated clays; additional antibacterial agents; coloring or whitening agents; preservatives; silicones; chlorophyl compounds; additional ammoniated material; etc.

Any suitable flavoring or sweetening materials may be employed in formulating a flavor for the dentifrice. Examples of flavoring constituents include the flavoring oils, e.g., oils of spearmint, peppermint, wintergreen, sassafras, clove, sage, eucalyptus, marjoram, cinnamon, lemon and orange, as well as sodium methylsalicylate. Suitable sweetening agents include sucrose, lactose, maltose, sorbitol, sodium cyclamate, perillartine and saccharine. Suitably, flavor and sweetening agents may together comprise from about 0.1 and 5% or more by weight of the compositions of the instant invention. The dentifrice may also contain a fluorine-containing compound having a beneficial effect on the care and hygiene of the oral cavity, e.g. diminution of enamel solubility in acid and protection of the teeth against decay. Examples include sodium fluoride, stannous fluoride, potassium fluoride, potassium stannous fluoride ($SnF_2$. KF), potassium fluorozirconate, sodium hexafluorostannate, stannous chlorofluoride, and sodium monofluorophosphate.

Prior art patents which deal with the inhibition of plaque or related dental problems are as follows:
- U.S. Pat. No. 3,928,618 Bauman
- U.S. Pat. No. 3,957,968 Cordon
- U.S. Pat. No. 4,089,943 Roberts et al.
- U.S. Pat. No. 4,100,269 Pader
- U.S. Pat. No. 4,132,771 Schreiber
- U.S. Pat. No. 4,156,715 Wagenknecht et al.

SUMMARY OF THE INVENTION

In general, the present invention pertains to oral compositions for dental use which contain, as one of the essential ingredients, a flavorant of the group peppermint oil, spearmint oil, cinnamon oil, and mixtures thereof; and which further contain, as another essential ingredient, cocoa powder. Although the preferred oral compositions of the invention are in the form of dentifrices, it will be understood that mouthwashes, chewing gums, lozenges, and the like are also encompassed. The flavorant is present in a dentifrice, for example, in an amount ranging from about 0.5 to 3% by weight, preferably from about 0.8 to 1.5%, while the amount of cocoa powder ranges from about 5 to 20% by weight, and preferably from about 8 to 15% by weight of the total composition.

The oral compositions of the invention are characterized by improved plaque inhibition or at least reduction in plaque formation.

An especially preferred oral composition of the invention not only contains the two anti-plaque essential ingredients, i.e. at least one of the prescribed flavorants and the cocoa powder, but utilizes only natural substances as components.

DETAILED DESCRIPTION OF THE INVENTION

In U.S. Pat. No. 4,156,715 to Wagenknecht, the disclosure of which is incorporated herein by reference, it is disclosed that certain essential oils previously employed in oral compositions for dental use have the ability to inhibit plaque formation. These essential oils are peppermint oil, cinnamon oil, spearmint oil as well as mixtures thereof. In accordance with the present invention it has now been found that cocoa powder also inhibits plaque formation and, furthermore, that the combination of the cocoa powder and one or more of the prescribed flavorants results in a novel anti-plaque oral composition for dental use. In addition, the ability to use the naturally occurring cocoa powder in conjunction with natural flavorants enables one to formulate an all natural oral composition having outstanding plaque inhibition properties by selecting available substances as the conventional components in, for example, toothpaste.

As set forth in U.S. Pat. No. 4,132,771 to Schreiber et al. taste and flavor are probably the most important single factor in consumer acceptance of an oral composition such as a dentifrice. The selection of acceptable sweetner and flavoring ingredients is therefore of significant importance in formulating a dentifrice.

Although chocolate flavor and aroma have almost universal appeal and would be an ideal candidate for oral compositions, chocolate itself cannot be employed as, for example, a dentifrice ingredient because of its high sugar content which causes tooth decay. In fact, material having a chocolate appearance or chocolate flavor would be contraindicated by conventional expectations. Nevertheless, it has already been reported that cocoa powder has exhibited a significant caries-inhibitory effect when added to cariogenic diets in animal studies. Although the exact mechanism of how the cocoa powder acts is unknown, there does appear to be a dose-related decrease in dextransucrase activity with increased cocoa powder concentrations in the diets. "The Effect of Cocoa on Dextransucrase Activity in *Streptacoccus mutans*" by V. J. Paolino et al., M.I.T. Dept. of Nutrition and Food Science. It has been found that cocoa powder in combination with certain flavoring oils can be effectively utilized to enhance the plaque inhibition properties of typical oral compositions for dental use and at the same time provide a highly desirable taste and flavor to the final composition.

Cocoa powder is one of the products obtained by the processing of cocoa beans, and more particularly it is derived from the kernel or fatty cotyledons of the bean known in the art as "nibs." Cocoa powders of varying fat contents may be employed for the present purposes, although it is preferred to use those having a fat content of from about 5 to about 60% by weight. For some purposes it is also possible to employ low-fat cocoa powder. The preparation of cocoa powder as well as analyses of various cocoa powders are described in detail in Kirk-Othmer, "Encyclopedia of Chemical Technology," published Interscience Publishers.

In general the amount of cocoa powder will range from about 0.5 to 25% by weight. For dentifrices, especially toothpastes, the amount of cocoa powder will be from 5 to 20% by weight, preferably 8 to 15% by weight.

Although cinnamon oil and spearmint oil may also be employed, the preferred essential oil is peppermint oil. It is employed in amounts ranging from about 0.05 to 10% by weight; and in toothpastes in amounts of from about 0.1 to 3% by weight, preferably about 0.8 to 1.5% by weight.

In addition to the cocoa powder and the prescribed flavoring oil, the toothpaste and dental creams of this invention will generally contain the following components:

|  | Ranges, % by Weight | |
|---|---|---|
|  | Broad | Preferred |
| (1) Abrasive or polishing agent | 10 to 70 | 20 to 60 |
| (2) Surfactant | 0.5 to 10 | 1 to 8 |
| (3) Binder | 1 to 15 | 2 to 10 |
| (4) Vehicle | 5 to 60 | 15 to 40 |
| (5) Foaming Agent plus water | 1 to 10 | 2 to 8 |
| (6) Fragrances | 0 to 3 | 0.5 to 2 |

As will be noted the use of a fragrance, a preferred fragrance for the present purposes being chocolate, is optional. For some applications, one can employ substances such as orris root in amounts of less than 5% by weight to mask any possible taste of soap.

When chewing gum is the oral composition then a natural or synthetic gum base in an amount ranging from about 10 to 95% by weight will be included. Natural gum bases include chicle, gutta percha, jelutong, balata, and the like as disclosed in column 7 of the U.S. Pat. No. 4,156,715. The synthetic gum bases include elastomers such as polyisobutylene, polyisoprene, isobutylene isoprene copolymers, copolymers of butadiene and styrene, and the like as also disclosed in said U.S. Pat. No. 4,156,715. However, it is preferred to use natural substances in formulating the oral compositions of this invention.

The abrasive or polishing agent may include such known materials as calcium carbonate, dicalcium diphosphate dihydrate, sodium metaphosphate, aluminum hydroxide, magnesium carbonate, calcium sulphate, silicas including aerogels and xerogels, tricalcium phosphate, and the like.

Useful vehicles include such conventional materials as glycerine, propylene glycol, polyethylene glycol 400, and the like.

The binder may be bentonite, starch, natural and synthetic gums, cellulose ethers, and similar materials well known to the art. The surface active agents or surfactants include castile soap, cocoa butter soap, etc.; although it will be understood that other conventional natural or synthetic surfactants may be employed.

Preferably natural foaming agents such as saponine or other known foaming agents generally useful for the present purposes may be utilized.

The invention will be more fully understood by reference to the following specific embodiment wherein the stated toothpaste formulation is composed of the following components:

|  | % by Weight |
|---|---|
| Cocoa Powder (10-12% butterfat) | 10.0 |
| Peppermint Oil | 1.0 |
| Glycerine | 36.6 |
| Bentonite | 4.3 |
| Calcium Carbonate | 33.3 |
| Castile Soap | 4.0 |
| Saponine plus H$_2$O | 5.3 |
| Fragrance (chocolate) | 1.2 |
| Orris Root | 4.3 |

EXAMPLE

Saliva was collected from two persons, thoroughly mixed, and divided into five Petri dishes. Two additional Petri dishes were filled with water as a control. Each of the 7 dishes received 3 scrupulously clean teeth each. All the teeth used had been scaled, polished, and debrided ultrasonically. They were caries free extracted human teeth.

The first dish contained teeth and New York City tap water. The second dish contained teeth and saliva. The third dish contained saliva, teeth, and natural oil of peppermint in a 1% concentration by weight. The fourth dish contained 10% cocoa by weight, saliva, and teeth. The fifth dish contained the toothpaste formulation delineated above, water, and teeth. The sixth dish contained the same toothpaste formulation, saliva, and teeth. The seventh dish contained 10% cocoa powder by weight, 1% oil of peppermint by weight, saliva, and teeth.

The study was conducted for a period of one month, at one week intervals, the results of plaque formation were checked by gross visual and tactile examination. The teeth in water did not collect any debris. The teeth in saliva with the anti-plaque ingredients remained in their pristine condition, whereas the teeth in saliva alone collected a substantial layer of slimy plaque which could be seem grossly and felt by tactile evaluation. Teeth in saliva and either in peppermint oil or cocoa powder, but not both, showed some plaque accumulation in contrast to no plaque accumulation when both peppermint oil and cocoa powder were employed. Five witnesses to this experiment were of the same opinion as to the gross difference between the treated and untreated teeth and the easily apparent total lack of debris on the teeth which were immersed in the toothpaste formulation with the anti-plaque ingredients.

The data shown above indicate that synergistic anti-plaque properties may result when the cocoa powder and certain flavorants such as peppermint oil are used together.

Although the present invention has been described above with respect to specific materials, it will be understood that it is subject to variations and modifications without departing from its broader scope. Thus, conventional toothpaste, mouthwash and chewing gum components can be employed in the usual amounts in formulating the improved compositions of this invention provided that a combination of cocoa powder and at least one of the prescribed flavorants is utilized.

What is claimed is:

1. In the art of inhibiting plaque accumulation on teeth by means of oral hygeine compositions containing effective plaque inhibiting amounts of either of (a) cocoa powder or (b) a flavorant selected from the group consisting of peppermint oil, spearmint oil, cinnamon oil, and mixtures thereof, the improvement which comprises the step of employing effective plaque inhibiting amounts of a combination of (a) and (b) in oral hygiene compositions characterized by improved plaque inhibition or at least reduction in plaque formation as contrasted to the degree of plaque accumulation obtained from separate employment of either of (a) or (b).

* * * * *